(12) United States Patent
Li et al.

(10) Patent No.: US 9,421,520 B2
(45) Date of Patent: Aug. 23, 2016

(54) PLATINUM/CARBON NANOTUBE CATALYST, THE PREPARATION PROCESS AND USE THEREOF

(75) Inventors: Can Li, Dalian (CN); Zhijian Chen, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 1342 days.

(21) Appl. No.: 13/201,233

(22) PCT Filed: May 11, 2010

(86) PCT No.: PCT/CN2010/000675
§ 371 (c)(1),
(2), (4) Date: Oct. 21, 2011

(87) PCT Pub. No.: WO2011/047523
PCT Pub. Date: Apr. 28, 2011

(65) Prior Publication Data
US 2012/0035388 A1    Feb. 9, 2012

(30) Foreign Application Priority Data
Oct. 21, 2009    (CN) .......................... 2009 1 0236390

(51) Int. Cl.
| | | |
|---|---|---|
| *C07C 67/30* | (2006.01) | |
| *B01J 23/42* | (2006.01) | |
| *B01J 37/34* | (2006.01) | |
| *B01J 21/18* | (2006.01) | |
| *B01J 37/02* | (2006.01) | |
| *B82Y 30/00* | (2011.01) | |
| *C07B 35/02* | (2006.01) | |
| *B01J 35/00* | (2006.01) | |
| *B01J 37/00* | (2006.01) | |
| *B01J 37/16* | (2006.01) | |

(52) U.S. Cl.
CPC .............. *B01J 23/42* (2013.01); *B01J 21/185* (2013.01); *B01J 35/0013* (2013.01); *B01J 37/009* (2013.01); *B01J 37/0201* (2013.01); *B01J 37/16* (2013.01); *B01J 37/343* (2013.01); *B82Y 30/00* (2013.01); *C07B 35/02* (2013.01); *C07C 67/30* (2013.01)

(58) Field of Classification Search
None
See application file for complete search history.

(56) References Cited

U.S. PATENT DOCUMENTS

2006/0142149 A1    6/2006    Ma et al.
2010/0298125 A1*   11/2010   Kim ....................... B01J 21/185
                                                     502/185

FOREIGN PATENT DOCUMENTS

| CN | 1559686 A | * | 1/2005 |
|---|---|---|---|
| CN | 1660487 | | 8/2005 |
| CN | 101456074 | | 6/2009 |
| CN | 101683624 | | 3/2010 |
| JP | 2006334527 | | 12/2006 |

OTHER PUBLICATIONS

Chen, Y. et al. "Method of depositing high density loading metal platinum on carbon nanometer pipe surface using oriented chemistry" CN 1559686 A (Jan. 5, 2005). English machine translation obtained Mar. 7, 2015 from the internet at <www.google.com>.*
Li et al. "Preparation and Characterization of Multiwalled Carbon Nanotube-Supported Platinum for Cathode Catalysts of Direct Methanol Fuel Cells" J. Phys. Chem. B 2003, 107, 6292-6299.*
Zhang et al. "Control method for carrying metal particles in carbon nanotube cavity or on external wall" CN101683624A (Mar. 31, 2010) English machine translation obtained Apr. 10, 2015 from the internet at <www.google.com>.*
Zhao et al. "Method for filling carbon nano tube with magnetic nano metal iron particles" CN101456074A (Jun. 17, 2009) English machine translation obtained Apr. 20, 2015 from the internet at <www.google.com>.*
Liu et al. "Preparation and Characterization of Platinum-Based Electrocatalysts on Multiwalled Carbon Nanotubes for Proton Exchange Membrane Fuel Cells" Langmuir 2002, 18(10), 4054-4060.*
Sigma-Aldrich "Nitric acid—ACS reagent, 70%" [online][retrieved on Apr. 10, 2015]. Retrieved from <www.sigmaaldrich.com>.*
Liu et al. "A parametric investigation of impregnation and drying of supported catalysts" Chem. Eng. Sci. 2008, 63, 4517-4530.*
International Search Report dated Jul. 7, 2010.

* cited by examiner

*Primary Examiner* — Nyeemah A Grazier
*Assistant Examiner* — Amanda L Aguirre
(74) *Attorney, Agent, or Firm* — Enshan Hong; VLP Law Group LLP

(57) ABSTRACT

This invention provides a platinum/carbon nanotube catalyst applicable to heterogeneous asymmetric hydrogenation, which is fabricated by supporting platinum on carbon nanotube carriers. The catalyst is prepared by the steps of: heating purified carbon nanotubes in nitric acid, filtering and washing the same with water until pH value of the filtrate becomes neutral, drying the carbon nanotubes; immersing the carbon nanotube carriers obtained in an aqueous chloroplatinic acid solution and carrying out ultrasonic treatment at room temperature; immersing the mixture of the carbon nanotubes and the aqueous chloroplatinic acid solution under stirring; drying the material by heating to 110° C. from room temperature and maintaining this temperature; grinding the product to fine powders, reducing the fine powders with an aqueous sodium formate solution under a heating condition, filtering and washing the product with deionized water, and drying the product. The invention further provides a process for preparing a platinum/carbon nanotube catalyst and a use thereof in heterogeneous asymmetric hydrogenation.

6 Claims, 2 Drawing Sheets

PLATINUM/CARBON NANOTUBE CATALYST, THE PREPARATION PROCESS AND USE THEREOF

PRIORITY CLAIM

This is a U.S. national stage of application No. PCT/CN10/000675, filed on May 11, 2010. Priority is claimed on the following application: China, Application No.: 200910236390.1 filed on Oct. 21, 2009, the content of which is incorporated here by reference.

TECHNICAL FIELD

The present invention relates to a platinum/carbon nanotube catalyst applicable to heterogeneous asymmetric hydrogenation, a preparation process for the above platinum/carbon nanotube catalyst, as well as a use of the above platinum/carbon nanotube catalyst.

BACKGROUND OF THE INVENTION

Since the 1990's, the demand for the chiral compounds of single enantiomers in the world has been very huge and increased year by year. At present, this demand focuses on the fields of medicine, agricultural chemicals and fine chemicals or the like. In the world medicine market, for example, the sale value of drugs of single enantiomers exceeded 172 billion $ in 2005, with an increasing rate of about 10% per year, and exceeded 200 billion $ in 2008. Among all the methods for obtaining the compounds of single enantiomers, asymmetric catalysis (homogeneous asymmetric catalysis and heterogeneous asymmetric catalysis) is very important and has been widely applied in various asymmetric syntheses.

Chiral alcohols are widely used important intermediates for chiral drugs, which can be obtained through the asymmetric hydrogenation of substrates containing functionalized keto-carbonyl group (such as ketoesters). In this research field, the following influential works have been reported. Baiker et al, in J. Mol. Catal., 1989, 49, 195 and J. Mol. Catal., 1990, 61, 207, reported the asymmetric hydrogenation of ethyl pyruvate for synthesizing chiral alcohols on a platinum-alumina catalyst, inwhich an enantioselectivity (ee value) they obtained was not more than 80%. Blaser et al, in Adv. Synth. Catal., 2003, 345, 45, reviewed the progresses including the heterogeneous asymmetric hydrogenation of α-ketoesters, and summarized all kinds of catalysts applied in heterogeneous asymmetric hydrogenation. Wherein, the catalyst with a code of E 4759 produced by Engelhard Co. and the catalyst with a code of 5R94 produced by Johnson Matthey Co. (both of them are commercial platinum-alumina catalysts) show relative good activity and optical selectivity in catalyzing the heterogeneous asymmetric hydrogenation of α-ketoesters. Until now, the researches on heterogeneous asymmetric hydrogenation of α-ketoesters in China and abroad have indicated that, among all kinds of catalysts composed of the carriers and chiral modifiers with various structures and functions researched in heterogeneous asymmetric hydrogenation, there have been no heterogeneous catalyst which is superior or comparable to the dominant commercial platinum-alumina catalysts in the international market when the reaction performance and stability are concerned.

Carbon nanotubes are novel nanomaterial with many unique properties, which possess excellent structure and mechanical performances, such as high strength, low density, high specific surface area, good electrical conductivity, and show broad application prospects in the field of composite functional materials, electronic industry, catalysis, energy conversions or the like. Carbon nanotubes are also one kind of excellent material for gas adsorption and hydrogen storage. Therefore, this invention carried out a research on heterogeneous asymmetric catalytic hydrogenation based on the novel material of carbon nanotubes, trying to achieve a novel progress and experience in the application of carbon nanotubes to heterogeneous catalytic hydrogenation, specifically, to heterogeneous asymmetric catalytic hydrogenation, and develop a novel platinum/carbon nanotube catalyst applicable to heterogeneous asymmetric hydrogenation.

SUMMARY OF THE INVENTION

An object of the invention is to provide a platinum/carbon nanotube catalyst applicable to heterogeneous asymmetric hydrogenation.

Another object of the invention is to provide a process for preparing the above platinum/carbon nanotube catalyst.

Still another object of the invention is to provide a use of the above platinum/carbon nanotube catalyst in the reaction of heterogeneous asymmetric hydrogenation.

In order to realize the objects described above, with regard to the platinum/carbon nanotube catalyst provided in the invention, the platinum nanoparticles can be loaded exclusively inside the tube cavities of carbon nanotubes, or can be loaded exclusively on the outer surfaces of the tube cavities of carbon nanotubes.

The platinum/carbon nanotube catalyst of the invention take carbon nanotubes as carriers. In the invention, it is considered that the platinum salt used has been completely reduced to metal platinum during the reaction, and thus, the formed platinum nanoparticles are 2-10 wt % based on the weight of the carbon nanotubes loaded with the platinum nanoparticles.

The invention provides a platinum/carbon nanotube catalyst wherein platinum nanoparticles are loaded inside the tube cavities of carbon nanotubes, which is prepared by the steps of:

1) preparing carbon nanotube carriers by treating purified carbon nanotubes in nitric acid with a concentration of 65-68 wt % at 110-160° C. for 4-16 hours, filtering and washing the carbon nanotubes with water until pH value of the filtrate becomes neutral, drying the carbon nanotubes at 50-120° C. so as to obtain functionalized carbon nanotube carriers;

2) immersing the carbon nanotube carriers obtained in step 1) in an aqueous chloroplatinic acid solution and carrying out ultrasonic treatment at room temperature for 1-4 hours;

3) immersing the mixture of the carbon nanotubes and the aqueous chloroplatinic acid solution obtained in step 2) under stirring for 12-60 hours;

4) drying the material obtained in step 3) slowly at a heating rate of 0.5° C./min from room temperature to 110° C. and keeping at 110° C. for 12-48 hours;

5) grinding the product obtained in step 4) to fine powders, reducing the fine powders with an aqueous sodium formate solution under a heating condition, filtering and washing the product with deionized water, and drying the product at 50-120° C. for 12-36 hours, so as to obtain a platinum/carbon nanotube catalyst wherein platinum nanoparticles are loaded inside the tube cavities of carbon nanotubes.

The invention provides a platinum/carbon nanotube catalyst wherein platinum nanoparticles are loaded on the outer surfaces of the tube cavities of carbon nanotubes, which is prepared by the steps of:

1) preparing carbon nanotube carriers by treating purified carbon nanotubes in nitric acid with a concentration of 65-68 wt % at 110-160° C. for 4-16 hours, filtering and washing the carbon nanotubes with water until pH value of the filtrate becomes neutral, drying the carbon nanotubes at 50-120° C. so as to obtain functionalized carbon nanotube carriers;

2) adding xylene to the carbon nanotube carriers under stirring and carrying out ultrasonic treatment for 1-4 hours;

3) adding an aqueous chloroplatinic acid solution to the product obtained in step 2) under stirring, and then adding deionized water, and stirring the product continuously for 15-30 minutes;

4) after adding an aqueous solution of sodium formate with a purity≥99.5 wt % to the product obtained in step 3), and performing reduction at 70-120° C. under stirring for 0.5-3 hours, cooling the product;

5) after cooling and layer separation, decanting a supernatant, adding absolute ethanol and stirring for dispersion, and carrying out separation;

6) dispersing the product obtained in step 5) into deionized water, filtering, and washing with water until pH value of the filtrate becomes neutral, drying at 50-120° C. so as to obtain a platinum/carbon nanotube catalyst wherein platinum nanoparticles are loaded on the outer surfaces of the tube cavities of carbon nanotubes.

The invention provides a process for preparing the above platinum/carbon nanotube catalyst wherein platinum nanoparticles are loaded inside the tube cavities of carbon nanotubes, which comprises the main steps of:

1) preparing carbon nanotube carriers by treating purified carbon nanotubes in nitric acid with a concentration of 65-68 wt % at 110-160° C. for 4-16 hours, filtering and washing the carbon nanotubes with water until pH value of the filtrate becomes neutral, drying the carbon nanotubes at 50-120° C. so as to obtain functionalized carbon nanotube carriers;

2) immersing the carbon nanotube carriers obtained in step 1) in an aqueous chloroplatinic acid solution and carrying out ultrasonic treatment at room temperature for 1-4 hours;

3) immersing the mixture of the carbon nanotubes and the aqueous chloroplatinic acid solution obtained in step 2) under stirring for 12-60 hours;

4) drying the material obtained in step 3) slowly at a heating rate of 0.5° C./min from room temperature to 110° C. and keeping at 110° C. for 12-48 hours;

5) grinding the product obtained in step 4) to fine powders, reducing the fine powders with an aqueous sodium formate solution under a heating condition, filtering and washing the product with deionized water, and drying the product at 50-120° C. for 12-36 hours, so as to obtain a platinum/carbon nanotube catalyst wherein platinum nanoparticles are loaded inside the tube cavities of carbon nanotubes.

The invention provides a process for preparing the above platinum/carbon nanotube catalyst wherein platinum nanoparticles are loaded on the outer surfaces of the tube cavities of carbon nanotubes, which comprises the main steps of:

1) preparing carbon nanotube carriers by treating purified carbon nanotubes in nitric acid at 110-160° C. for 4-16 hours, filtering and washing the carbon nanotubes with water until pH value of the filtrate becomes neutral, drying the carbon nanotubes at 50-120° C. so as to obtain functionalized carbon nanotube carriers;

2) adding xylene to the carbon nanotube carriers under stirring and carrying out ultrasonic treatment for 1-4 hours;

3) adding an aqueous chloroplatinic acid solution to the product obtained in step 2) under stirring, and then adding deionized water, and stirring the product continuously for 15-30 minutes;

4) adding sodium formate to the product obtained in step 3) to perform reduction at 70-120° C. under stirring for 0.5-3 hours, and cooling the product;

5) after cooling and layer separation, decanting a supernatant, adding absolute ethanol and stirring for dispersion, and carrying out separation;

6) dispersing the product obtained in step 5) into deionized water, filtering, and washing with water until pH value of the filtrate becomes neutral, drying at 50-120° C. so as to obtain a platinum/carbon nanotube catalyst wherein platinum nanoparticles are loaded on the outer surfaces of the tube cavities of carbon nanotubes.

When a catalyst wherein platinum is loaded inside carbon nanotubes is prepared, an aqueous solution of platinum salt, that is, an aqueous chloroplatinic acid solution, is directly used for ultrasonic treatment and immersing. By utilizing the effects of adsorption and enrichment of the capillary forces of carbon nanotubes with open ends (the open ends are obtained by oxidation with nitric acid) for chloroplatinic acid in the aqueous solution, chloroplatinic acid in the aqueous solution is sufficiently or even completely enriched inside the tube cavities of carbon nanotubes after a relative long-time impregnation course. Thus, platinum nanoparticles prepared by reduction are encapsulated inside the tube cavities of carbon nanotubes.

When the platinum/carbon nanotube catalyst wherein platinum nanoparticles are loaded on the outer surfaces of the tube cavities of carbon nanotubes is prepared, firstly, the carbon nanotube carriers are dispersed with an organic solvent of xylene under a condition of ultrasonic treatment. This operation makes the interior of the tube cavities of carbon nanotubes and the spaces between the nanostructures of the carbon nanotubes fully filled by the hydrophobic solvent, xylene. Thus, when a short-time impregnation is carried out by introducing an aqueous chloroplatinic acid solution, the interior of the tube cavities of carbon nanotubes is fully filled by the hydrophobic solvent, xylene, which prevents the aqueous chloroplatinic acid solution from entering the interior of the nanotube cavities of carbon nanotubes and therefore preventing the impregnation course of chloroplatinic acid in the nanotube cavities of carbon nanotubes. Under a condition of relative short-time stirring, the impregnation course of the aqueous chloroplatinic acid solution only happens on the outer surface of the carbon nanotubes accessible easily. Thus, after reduction, the platinum/carbon nanotube catalyst wherein platinum nanoparticles are loaded exclusively on the outer surfaces of the tube cavities of carbon nanotubes is prepared. The use of ethanol in the following steps is mainly to extract, wash and remove the oily solvent, xylene. Finally, the prepared catalyst is washed with deionized water.

When the catalyst wherein platinum is loaded inside carbon nanotubes is prepared, the capillary adsorption effect of the tube cavities of carbon nanotubes for the platinum metal precursor (chloroplatinic acid) in the aqueous solution is utilized to enrich chloroplatinic acid inside the tube cavities of carbon nanotubes under the capillary forces. Thus, the catalyst wherein platinum is loaded inside carbon nanotubes is prepared. When the catalyst wherein platinum nanoparticles are loaded on the outer surfaces of the tube cavities of carbon nanotubes is prepared, the tube cavities of the carbon nanotube carriers are filled with a hydrophobic solvent, xylene firstly. This operation eliminates or prevents the capillary adsorption effect for the aqueous chloroplatinic acid solution so that the impregnation course only happens on the outer surface of the carbon nanotubes accessible easily. Thus, the catalyst wherein platinum nanoparticles are loaded exclusively on the outer surfaces of the tube cavities of carbon nanotubes is prepared.

The carbon nanotubes used in the invention are single-wall carbon nanotubes or multi-wall carbon nanotubes, wherein the inner diameter of the single-wall carbon nanotube is 2-15 nm, the outer diameter thereof is 2-15 nm, and the inner diameter of the multi-wall carbon nanotube is 2-15 nm, the outer diameter thereof is 8-60 nm.

The concentration of the aqueous chloroplatinic acid solution used in the invention is 0.8-10 mg Pt/ml. The amount of the aqueous chloroplatinic acid solution as compared with the carbon nanotubes is 5-60 ml/g.

An ultrasonic oscillator is used for the ultrasonic treatment in the invention, wherein the output power of the ultrasonic oscillator is 120-1000 W, the working frequency thereof is 40-60 KHz.

The concentration of the aqueous sodium formate solution used in the invention is 24-42 mg/ml, and the mole ratio of sodium formate to the reduced platinum is 10-20:1.

The platinum/carbon nanotube catalyst of the invention is used for the asymmetric hydrogenation of α-ketoester substrates under the modification of a chiral modifier. The reaction conditions are as follows: temperature 0-35° C., stirring speed 400-1800 rpm, hydrogen pressure 1.0-10 MPa. The substrates are α-ketoesters, and the formula of α-ketoesters is $R_1C(O)C(O)OR_2$, in which $R_1$ is $CH_3-$, $C_6H_5-$ or $C_6H_5(CH_2)_3-$; $R_2$ is $CH_3-$ or $C_2H_5-$. The solvent is one or two selected from the group consisting of methanol, ethanol, acetic acid, toluene, dichloromethane and tetrahydrofuran.

Before use, the platinum/carbon nanotube catalyst of the invention should be pretreated in a hydrogen gas stream at 200-400° C. for 1.5-2 hours.

The characters of the platinum/carbon nanotube catalysts in the invention can be summarized as follows: mild conditions, convenient preparation, concisely controlled preparation of the size and the location of platinum nanoparticles, such as the well-controlled preparation of platinum nanoparticles uniformly distributed inside the nanochannels of carbon nanotubes with the size of 2-4 nm. Compared with the existing various catalysts for the heterogeneous asymmetric hydrogenation of various α-ketoesters (including various types of the commercial platinum-almuina catalysts and the commercial platinum-active carbon catalysts), the platinum-carbon nanotube catalysts prepared in the invention exhibit obviously much higher reactivity and relatively higher or equal enantioselectivity.

DETAILED DESCRIPTION OF THE PRESENTLY PREFERRED EMBODIMENTS

Figure 1:
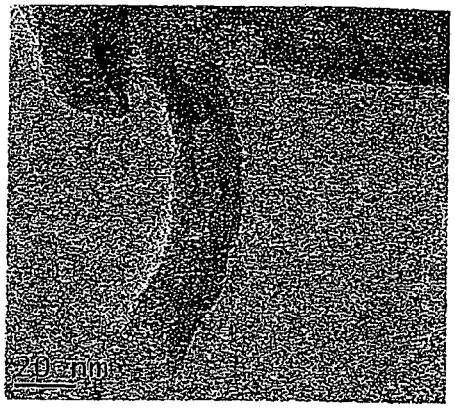
FIGS. 1-2 are photographs by transmission electron microscope (TEM) of the prepared platinum/carbon nanotube catalysts Pt-in-CNTs (the platinum particles are loaded inside the tube cavities of carbon nanotubes, wherein the rulers in both figures are the same, that is, 20 nm).

The preparation of the platinum/carbon nanotube catalysts and the asymmetric hydrogenation reaction according to the invention are described in details respectively as follows:

1) The Preparation of Carbon Nanotube Carriers

Purified carbon nanotubes with a certain geometrical shape are treated with concentrated nitric acid (65-68 wt %), heated under stirring for 4-16 h at a heating temperature of 110-160° C. Then, the carbon nanotubes are filtered and washed with water until pH value of the filtrate becomes neutral, and dried in a drier at 50-120° C. for 12-24 h to obtain black carriers of functionalized carbon nanotubes. These functionalized carbon nanotubes are used for preparing a platinum/carbon nanotube catalyst wherein platinum nanoparticles are loaded inside the tube cavities of carbon nanotubes (denoted by Pt-in-CNTs) and a platinum/carbon nanotube catalyst wherein platinum nanoparticles are loaded on the outer surfaces of the tube cavities of carbon nanotubes (denoted by Pt-out-CNTs).

2) Immersion with Ultrasonic Treatment

The functionalized carbon nanotube carriers are immersed in an aqueous chloroplatinic acid solution at a certain concentration and ultrasonic treated at room temperature in an ultrasonic oscillator for 1-4 h.

The carbon nanotube carriers to be immersed can be single-wall carbon nanotubes, double-wall carbon nanotubes, or multi-wall carbon nanotubes. In view of the applicability of preparation, economy and the scope of application, the multi-wall carbon nanotubes are preferable.

The concentration of the aqueous chloroplatinic acid solution used for immersion is 0.8-10 mg Pt/ml. The amount of the aqueous solution as compared with the carbon nanotubes is 5-60 ml/g. Based on the mass of platinum metal, the addition amount of chloroplatinic acid used for immersion is in a loading amount of 2-10%, generally, a loading amount of about 5%. The output power of the ultrasonic oscillator for immersion with ultrasonic treatment is 120-1000 W, the working frequency thereof is 40-60 KHz.

3) Immersion Under Stirring

The mixture of the carbon nanotubes and the aqueous chloroplatinic acid solution obtained in step 2) is put into a glass container (such as, a flask), immersed under stirring for 12-60 hours.

4) Controlled Drying

The material obtained in step 3) is slowly dried at a heating rate of 0.5° C./min from room temperature to 110° C. and kept at 110° C. for 12 h-48 h to obtain a black solid.

5) Reduction

The dried black solid obtained in step 4) is crushed and ground to fine powders. The catalyst precursor is reduced with an aqueous sodium formate solution at a certain concentration under heating. After the reduction, the product is filtered, washed with deionized water and dried in a drier at 50-120° C. for 12-36 h.

By the preparation process of steps 1-5, the platinum/carbon nanotube catalyst wherein platinum nanoparticles are assembled inside the tube cavities of carbon nanotubes (denoted by Pt-in-CNTs) is obtained.

The concentration of the aqueous sodium formate solution used for reduction is 24-42 mg/ml, and the mole ratio of sodium formate to the reduced platinum is 10-20:1. The heating manner used in the reduction is oil bath heating at a temperature of 70-120° C.

The reduction time is 30-180 min.

The process for preparing the platinum/carbon nanotube catalyst wherein platinum nanoparticles are loaded on the outer surfaces of the tube cavities of carbon nanotubes (denoted by Pt-out-CNTs) is described below, which mainly comprises the steps of:

1) preparing carbon nanotube carriers by treating purified carbon nanotubes in nitric acid at 110-160° C. for 4-16 hours, filtering and washing the carbon nanotubes with water until pH value of the filtrate becomes neutral, drying the carbon nanotubes at 50-120° C. so as to obtain functionalized carbon nanotube carriers;

2) adding xylene to the carbon nanotube carriers under stirring and carrying out ultrasonic treatment for 1-4 hours;

3) adding an aqueous chloroplatinic acid solution to the product obtained in step 2) under stirring, and then adding deionized water, and stirring the product continuously for 15-30 minutes;

4) adding sodium formate to the product obtained in step 3) to perform reduction at 70-120° C. under stirring for 0.5-3 hours, and cooling the product; wherein the mole ratio of sodium formate to the reduced platinum is 10-20:1, and the heating manner used in the reduction is oil bath heating at a temperature of 70-120° C.;

5) after cooling and layer separation, decanting a supernatant, adding absolute ethanol and stirring for dispersion, and carrying out separation;

6) dispersing the product obtained in step 5) into deionized water, filtering, and washing with water until pH value of the filtrate becomes neutral, drying at 50-120° C. so as to obtain a platinum/carbon nanotube catalyst wherein platinum nanoparticles are loaded on the outer surfaces of the tube cavities of carbon nanotubes.

The above catalysts are applied in the asymmetric hydrogenation according to the following steps:

The dried catalyst prepared in the steps described above is pretreated in a hydrogen gas stream firstly, then modified by a chiral modifier and applied to the heterogeneous asymmetric hydrogenation of α-ketoester substates under a certain hydrogen pressure, and very high reactivity and enantioselectivity can be obtained.

Before use, the catalyst should be pretreated in a hydrogen gas stream at 200-400° C. for 1.5-2 h. The chiral modifier is a natural alkaloid, such as cinchonidine or dihydrocinchonidine, and can also be other cinchona alkaloids with optical activity.

The asymmetric hydrogenation is carried out in an autoclave reactor at a temperature of 0-35° C., a stirring speed of 400-1800 rpm and a hydrogen pressure of 1.0-10 MPa. When the hydrogen pressure does not change any longer, the asymmetric hydrogenation reaction reaches the end. The mole ratio of the substrate to the catalyst is 12000-200:1. The substrates are α-ketoesters, and the formula of α-ketoesters is $R_1C(O)C(O)OR_2$, in which $R_1$ is $CH_3$—, $C_6H_5$— or $C_6H_5(CH_2)_3$—; $R_2$ is $CH_3$— or $C_2H_5$—. The solvent is one or two selected from the group consisting of methanol, ethanol, acetic acid, toluene, dichloromethane and tetrahydrofuran.

The asymmetric hydrogenation of α-ketoester substrates (such as ethyl pyruvate and methyl pyruvate) catalyzed by the chiral modifier-modified platinum/carbon nanotube (Pt-in-CNTs) catalyst can achieve very high enantioselectivity (ee value of 80-96%) and activity (TOF can be up to $6-12 \times 10^4 \, h^{-1}$ or more).

The whole process is illustrated through the examples in detail below, however, the scopes of the claims of the invention is not limited to these examples. At the same time, the examples only present part of the conditions to realize the goal of the invention, but it's not absolutely necessary to satisfy these conditions to realize the goal of the invention.

Example 1

The Preparation of Functionalized Carbon Nanotube Carriers 4.0 g purified carbon nanotubes (average inner diameter 4-8 nm, outer diameter 10-20 nm) (multi-wall carbon nanotubes, a product from Times Nano Co., Chengdu, China) were weighed and put into a 250 mL round bottom flask. A magnetic stirring bar was put into the flask. 200 ml concentrated nitric acid (65-68%) was added. The flask was equipped with a reflux condenser, heated to 110-160° C. in an oil bath, stirred for 4-16 hours, and cooled. The carbon nanotubes were filtered and washed with deionized water until pH value of the filtrate became neutral. Then, the carbon nanotubes were dried in an oven at 50-120° C. for 12-24 h. Thus, the functionalized carbon nanotube carriers were obtained.

Example 2

The Preparation of a Platinum/Carbon Nanotube Catalyst Wherein Platinum Nanoparticles are Loaded Inside the Tube Cavities of Carbon Nanotubes 1) In a round bottom flask, 2.72 ml of an aqueous chloroplatinic acid solution (with a concentration of 18.5 mg Pt/ml, 5% Pt loading amount) was added into 20 ml of deionized water, and mixed uniformly by magnetic stirring. Then, 1.0 g the dried carbon nanotube carriers (which had been functionalized) were added and ultrasonic treated in an ultrasonic oscillator for 1-4 h.

2) The mixture was continuously immersed for 12 h or more under stirring.

3) The material obtained in step 2) was dried slowly at a heating rate of 0.5° C./min from room temperature to 110° C. and keeping at 110° C. for 48 hours.

4) The catalyst precursor obtained in step 3) was reduced in an aqueous sodium formate solution (the addition amount of sodium formate was about 10-20 times more than the molar amount of the loaded platinum, 70-120° C.). After the reduction, the product was filtered, washed with deionized water, and dried in a dryer at 50-120° C. for 12-36 hours.

Figure 2:
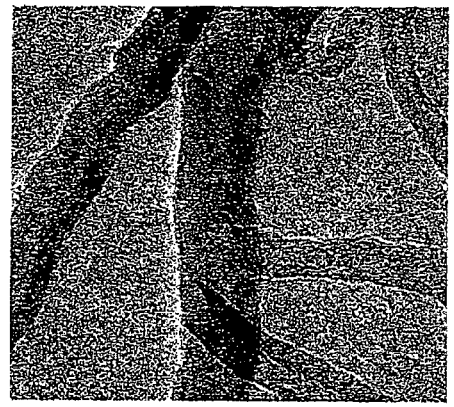

By the preparation process with steps 1-4, the platinum/carbon nanotube catalyst wherein platinum nanoparticles are assembled inside the tube cavities of carbon nanotubes (denoted by Pt-in-CNTs-1) was obtained. The platinum/carbon nanotube catalyst was characterized by transmission electron microscopy (TEM) (the carriers were multi-wall carbon nanotubes, a product from Times Nano Co., Chengdu, China) (FIGS. 1-2 were the photographs thereof by transmission electron microscope), wherein the particle diameter of the formed platinum nanoparticles was 2-4 nm.

Example 3

This procedure was exactly analogous to that described in Example 2, except that the size of the functionalized carbon nanotube carrier was changed to outer diameter 8 nm and inner diameter 3-4 nm. The preparation process of the functionalized carbon nanotube carriers was similar to that in Example 1. The catalyst prepared was denoted by Pt-in-CNTs-2.

Example 4

The Preparation of a Platinum/Carbon Nanotube Catalyst Wherein Platinum Nanoparticles are Loaded on the Outer Surfaces of the Tube Cavities of Carbon Nanotubes 1) 1.0 g dried carbon nanotube carriers (which had be functionalized) (average inner diameter 4-8 nm, outer diameter 10-20 nm) (the carriers were multi-wall carbon nanotubes, a product from Times Nano Co., Chengdu, China) were weighed and put into a 50 ml round bottom flask. The flask was added with 20 g (about 23.3 ml) xylene under stirring and then ultrasonic treated in an ultrasonic oscillator for 2-4 h.

2) To the mixture obtained in step 1), 2.72 ml of an aqueous chloroplatinic acid solution (with a concentration of 18.5 mg Pt/ml), then 5.7 ml deionized water were added, and then the mixture was stirred for 15-30 min.

3) Sodium formate (%, 362.4 mg) was added to the mixture to carry out reduction under stirring.

4) A supernatant was decanted after layer separation, the residue was added with 40 ml absolute ethanol and stirred for 10 min. After separation by centrifugation, the clear solution was separated and the carbon nanotube catalyst was washed with 40 ml absolute ethanol, then centrifuged and separated. The catalyst was washed with absolute ethanol for 4-5 times in this manner (in order to remove xylene by washing).

5) The carbon nanotube catalyst obtained in step 4) was re-dispersed into deionized water, filtered, and washed with deionized water until pH value of the filtrate became neutral, and then dried.

Figure 3:
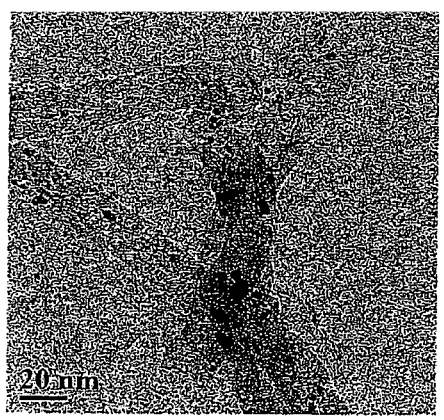
FIGS. 3-4 are photographs by transmission electron microscope of the prepared platinum/carbon nanotube catalysts Pt-out-CNTs (the platinum particles are loaded outside of the tube cavities of carbon nanotubes, wherein the rulers in both figures are the same, that is, 20 nm).
Figure 4:
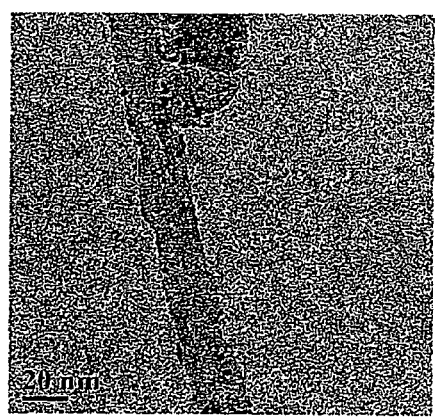

By the preparation process with steps 1-5, the platinum/carbon nanotube catalyst wherein platinum nanoparticles are loaded on the outer surfaces of the tube cavities of carbon nanotubes was obtained (FIGS. 3-4 were the photographs thereof by transmission electron microscopy). The prepared catalyst was denoted by Pt-out-CNTs. The particle diameter of the platinum nanoparticles loaded on the outer surfaces of the tube cavities of carbon nanotubes was 2-4 nm.

Example 5

Figure 5:
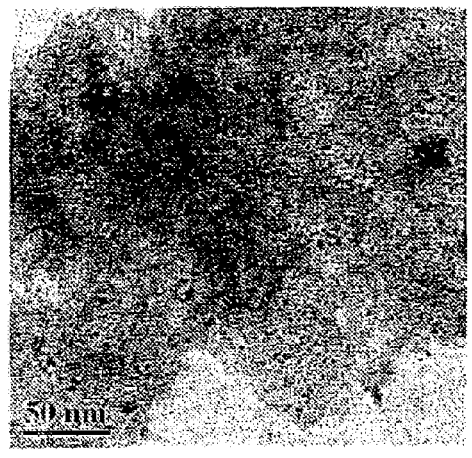
FIG. 5 is a photograph by transmission electron microscope of a 5% Pt/C catalyst prepared in laboratory.

A commercial active carbon (GH-16 Active Carbon, BET specific surface area: ~1100 $m^2/g$, pore volume: 0.607 mL/g, a product from Beijing Guanghua Woods Plant, which had been functionalized according to the manner for treating carbon nanotubes) was selected as the carriers. 2.72 ml of an aqueous chloroplatinic acid solution (with a concentration of 18.5 mg Pt/ml, 5% Pt loading amount) was added into 20 ml of deionized water, and mixed uniformly by magnetic stirring. Then, 1.0 g the dried active carbon carriers were added and immersed for 4-5 h under magnetic stirring, and then dried at 110° C. for 48 h. The platinum/active carbon catalyst precursor was reduced according to the method in step 4) in Example 2. A loaded platinum/active carbon catalyst was obtained after filtering and washing. The obtained catalyst was denoted by Pt/C (Lab.). FIG. 5 was the photograph thereof by transmission electron microscopy.

Example 6

Figure 6:
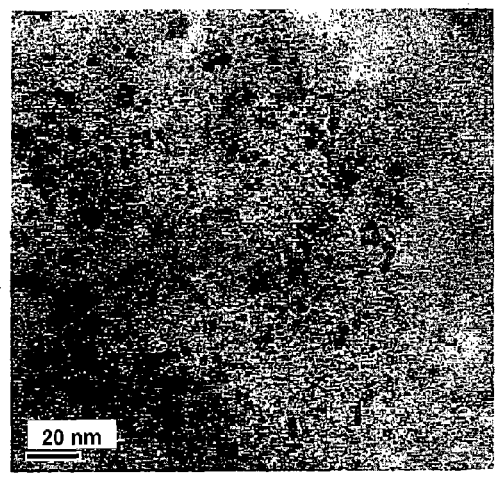
FIG. 6 is a photograph by transmission electron microscope of a commercial 5% Pt/C catalyst.

A commercial platinum/carbon catalyst (5% Pt loading amount) (a 5% platinum/active carbon catalyst, a product from Shanxi Kaida Chemical Industry Company, product series NO. 202, China) is purchased for reaction. The catalyst was denoted by Pt/C. FIG. 6 was the photograph thereof by transmission electron microscopy.

Example 7

The Heterogeneous Asymmetric Hydrogenation of Ethyl Pyruvate 1) 20 mg of the Pt-in-CNTs-1 catalyst prepared in Example 2 was weighed and pretreated in a hydrogen gas stream at 225° C. for 2 h.

2) Then, 0.20 ml of ethyl pyruvate, 4 ml of acetic acid, 20 mg of the pretreated catalyst, and 4.0 mg of cinchonidine were added into a reaction container in a 100 ml autoclave, and the autoclave was sealed.

3) The autoclave sealed in step 2) was purged with hydrogen gas, and then introduced with high purity hydrogen gas at about 6.50 MPa. An asymmetric hydrogenation was carried out under magnetic stirring. The reaction was stopped after 3 min at room temperature. The catalyst was separated from the liquid product by centrifugation. The product was analyzed on a chiral gas chromatograph column (HP19091G-B213, 30 m×0.32 mm×0.25 um, Agilent Co.). The conversion was 100%, and the enantiomeric excess(ee) value was 92%.

Example 8

The Heterogeneous Asymmetric Hydrogenation of Ethyl Pyruvate

This procedure was exactly analogous to that described in Example 7, except that the pretreatment condition of step 1 in Example 7 was changed, that is, the Pt-in-CNTs-1 catalyst was pretreated at 400° C. for 2 h. The conversion was 100%, and the ee value of the hydrogenation products was 90%.

Example 9

The Heterogeneous Asymmetric Hydrogenation of Ethyl Pyruvate

The procedure was exactly analogous to that described in Example 7, except that the catalyst used in step 1 of Example 7 was changed to the Pt-in-CNTs-2 catalyst prepared in Example 3. The conversion was 100%, and the ee value of the hydrogenation products was 88%.

Example 10

The Heterogeneous Asymmetric Hydrogenation of Ethyl Pyruvate

The procedure was exactly analogous to that described in Example 7, except that the catalyst used in step 1 of Example 7 was changed to the Pt-out-CNTs catalyst prepared in Example 4, and the reaction time in step 3 of Example 7 was change to be 25 min. The conversion was 99.3%, and the ee value of the hydrogenation products was 75.2%.

Example 11

The Heterogeneous Asymmetric Hydrogenation of Ethyl Pyruvate

The procedure was exactly analogous to that described in Example 10, except that the catalyst used was the Pt-out- CNTs catalyst prepared in Example 4, and the reaction time in step 3 of Example 10 was change to be 12 min. The conversion was 84.9%, and the ee value of the hydrogenation products was 75.1%.

Example 12

The Heterogeneous Asymmetric Hydrogenation of Ethyl Pyruvate

The procedure was exactly analogous to that described in Example 10, except that the catalyst used was the Pt-out-CNTs catalyst prepared in Example 4, and the reaction time in step 3 of Example 10 was change to be 6 min. The conversion was 32.5%, and the ee value of the hydrogenation products was 69.4%.

Example 13

The Heterogeneous Asymmetric Hydrogenation of Ethyl Pyruvate

The procedure was exactly analogous to that described in Example 7, except that the catalyst used in step 1 of Example 7 was changed to the Pt/C(Lab.) catalyst prepared in Example 5, and the reaction time in step 3 of Example 7 was change to be 15 min. The conversion was 30%, and the ee value of the hydrogenation products was 52%.

Example 14

The Heterogeneous Asymmetric Hydrogenation of Ethyl Pyruvate

The procedure was exactly analogous to that described in Example 7, except that the catalyst used in step 1 of Example 7 was changed to the commercial Pt/C catalyst obtained in Example 6, and the reaction time in step 3 of Example 7 was change to be 30 min. The conversion was 99%, and the ee value of the hydrogenation products was 54%.

Example 15

The Heterogeneous Asymmetric Hydrogenation of Ethyl Pyruvate 1) 10 mg Pt-in-CNTs-1 catalyst was weighed and pretreated in a hydrogen gas stream at 225° C. for 2 h.
2) 10 mg of the pretreated catalyst and 2 ml of acetic acid were added into a reaction container in a 100 ml autoclave, and the autoclave was pre-hydrogenated for 5-15 min. Then other materials were introduced. The autoclave was sealed.
3) The autoclave sealed in step 2) was purged with hydrogen gas, and then introduced with high purity hydrogen gas at about 5.0 MPa. An asymmetric hydrogenation was carried out under magnetic stirring. After the reaction, the catalyst was separated from the liquid product by centrifugation. The product was analyzed on a chiral gas chromatograph column (HP19091G-B213, 30 m×0.32 mm×0.25 um, Agilent Co.). The conversion was 100%, and the ee value was 95%.

Example 16

The heterogeneous asymmetric hydrogenation of ethyl 2-oxo-4-phenyl-butyrate (EOPB)

The procedure was exactly analogous to that described in Example 7, except that: the catalyst was 10 mg Pt-in-CNTs-1 obtained in Example 2, the substrate in step 2 of Example 7 was changed to 0.10 ml ethyl 2-oxo-4-phenyl-butyrate, the reaction time in step 3 of Example 7 was change to be 6 min, and the hydrogen pressure was changed to 5.8 MPa. The conversion was 98.3%, and the ee value of the hydrogenation products was 86.4%.

Example 17

The heterogeneous asymmetric hydrogenation of ethyl 2-oxo-4-phenyl-butyrate (EOPB)

The procedure was exactly analogous to that described in Example 7, except that: the catalyst used was changed to 10 mg commercial 5% $Pt/Al_2O_3$ catalyst (E 4759, Engelhard Co.) pretreated in a hydrogen gas stream at 400° C. for 2 h, the substrate used in step 2 of Example 7 was changed to 0.10 ml ethyl 2-oxo-4-phenyl-butyrate, the reaction time in step 3 of Example 7 was change to be 60 min, and the hydrogen pressure was changed to 5.8 MPa. The conversion was 98.3%, and the ee value of the hydrogenation products was 83.0%.

Example 18

The Heterogeneous Asymmetric Hydrogenation of Ethyl Pyruvate 1) 20 mg commercial 5% $Pt/Al_2O_3$ catalyst was weighed and pretreated in a hydrogen gas stream at 400° C. for 2 h.
2) Then, as the operations in step 2 of Example 7, 0.20 ml of ethyl pyruvate, 4 ml of acetic acid, 20 mg of the pretreated catalyst, and 4.0 mg of cinchonidine were added into a reaction container in a 100 ml autoclave, and the autoclave was sealed.
3) The autoclave sealed in step 2) was purged with hydrogen gas, and then introduced with high purity hydrogen gas at about 6.50 MPa. An asymmetric hydrogenation was carried out under magnetic stirring. The reaction was stopped after 18 min at room temperature. The catalyst was separated from the liquid product by centrifugation. The product was analyzed on a chiral gas chromatograph column. The conversion was 99.3%, and the ee value was 90.1%.

Example 19

The Heterogeneous Asymmetric Hydrogenation of Ethyl Pyruvate

1) The operation was exactly analogous to that of step 1 in Example 17, except that 10 mg commercial 5% $Pt/Al_2O_3$ catalyst was pretreated in a hydrogen gas stream at 400° C. for 2 h.
2) The operation was exactly analogous to that of step 2 in Example 17, except that the amounts of reactants were reduced to half according to the amount of the catalyst. That is, 0.10 ml of ethyl pyruvate, 2 ml of acetic acid, 10 mg of the pretreated catalyst, and 2.0 mg of cinchonidine were used.
3) The autoclave sealed in step 2) was purged with hydrogen gas, and then introduced with high purity hydrogen gas at about 6.50 MPa. An asymmetric hydrogenation was carried out under magnetic stirring. The reaction was stopped after 5 min at room temperature. The catalyst was separated from the liquid product by centrifugation. The product was analyzed on a chiral gas chromatograph column. The conversion was 80.6%, and the ee value was 88.7%.

Example 20

1) The operation was exactly analogous to that of step 1 in Example 17, except that 10 mg commercial 5% Pt/Al$_2$O$_3$ catalyst was pretreated in a hydrogen gas stream at 400° C. for 2 h.

2) The operation was exactly analogous to that of step 2 in Example 17, except that 5 mg of cinchonidine, 0.10 ml of ethyl pyruvate, 10 mg of the pretreated catalyst, 2 ml of acetic acid were used.

3) The autoclave sealed in step 2) was purged with hydrogen gas, and then introduced with high purity hydrogen gas at about 6.50 MPa. An asymmetric hydrogenation was carried out under magnetic stirring. The reaction was stopped after 200 seconds at room temperature. The catalyst was separated from the liquid product by centrifugation. The product was analyzed on a chiral gas chromatograph column. The conversion was 91.8%, and the ee value was 89.8%.

Example 21

The Heterogeneous Asymmetric Hydrogenation of Ethyl Pyruvate

1) The operation was exactly analogous to that of step 1 in Example 17, except that 10 mg Pt-in-CNTs-1 catalyst was pretreated in a hydrogen gas stream at 225° C. for 2 h.

2) The operation was exactly analogous to that of step 2 in Example 17, except that the amounts of reactants were reduced to half according to the amount of the catalyst. The addition amount of cinchonidine was 2 mg.

3) The autoclave sealed in step 2) was purged with hydrogen gas, and then introduced with high purity hydrogen gas at about 6.50 MPa. An asymmetric hydrogenation was carried out under magnetic stirring. The reaction was stopped after 2 min at room temperature. The catalyst was separated from the liquid product by centrifugation. The product was analyzed on a chiral gas chromatograph column. The conversion was 96.0%, and the ee value was 91.6%.

Example 22

The Heterogeneous Asymmetric Hydrogenation of Methyl Pyruvate

The procedure was exactly analogous to that of Example 7. The catalyst was Pt-in-CNTs-1 catalyst pretreated in a hydrogen gas stream at 225° C. for 2 h. The conversion was 100%, and the ee value of the hydrogenation products was 93%.

In summary, by the functionalization of carbon nanotube materials and the special preparation methods developed in this invention, platinum nanoparticles are assembled exclusively inside the tube cavities of carbon nanotubes, or loaded exclusively on the outer surfaces of the tube cavities of carbon nanotubes, and the size (a diameter of 2-4 nm) and distribution of platinum nanoparticles can be well controlled. Compared with the existing various catalysts for the heterogeneous asymmetric hydrogenation of various α-ketoesters (including various types of the commercial platinum-almuina catalysts and the commercial platinum-active carbon catalysts), the platinum-carbon nanotube catalysts prepared in the invention exhibit obviously much higher reactivity and relatively higher or equal enantioselectivity. Thus, they show very captivating commercial applications and prospects.

What is claimed is:

1. A process for preparing a platinum/carbon nanotube catalyst wherein platinum nanoparticles are exclusively loaded inside the tube cavities of carbon nanotubes, comprising steps of:
    1) preparing carbon nanotube carriers by treating purified carbon nanotubes in nitric acid with a concentration of 65-68 wt % at 110-160° C. for 4-16 hours, filtering and washing the carbon nanotubes with water until pH value of the filtrate becomes neutral, drying the carbon nanotubes at 50-120° C. so as to obtain functionalized carbon nanotube carriers;
    2) immersing the carbon nanotube carriers obtained in step 1) in an aqueous chloroplatinic acid solution and carrying out ultrasonic treatment at room temperature for 1-4 hours;
    3) stirring the mixture of the carbon nanotubes and the aqueous chloroplatinic acid solution obtained in step 2) for 12-60 hours;
    4) drying the material obtained in step 3) slowly at a heating rate of 0.5° C./min from room temperature to 110° C. and keeping at 110° C. for 12-48 hours; and
    5) grinding the product obtained in step 4) to fine powders, reducing the fine powders with an aqueous sodium formate solution under a heating condition, filtering and washing the product with deionized water, and drying the product at 50-120° C. for 12-36 hours, so as to obtain a platinum/carbon nanotube catalyst wherein platinum nanoparticles are loaded inside the tube cavities of carbon nanotubes.

2. The process as claimed in claim 1, wherein the carbon nanotubes are single-wall carbon nanotubes or multi-wall carbon nanotubes.

3. The process as claimed in claim 1, wherein the concentration of the aqueous chloroplatinic acid solution is 0.8-10 mg Pt/ml, and the amount of the aqueous chloroplatinic acid solution as compared with the carbon nanotubes is 5-60 ml/g.

4. The process as claimed in claim 1, wherein an ultrasonic oscillator is used for the ultrasonic treatment, wherein the output power of the ultrasonic oscillator is 120-1000 W, the working frequency thereof is 40-60 KHz.

5. The process as claimed in claim 1, wherein the concentration of the aqueous sodium formate solution is 24-42 mg/ml, and the mole ratio of sodium formate to the reduced platinum is 10-20:1.

6. The process of claim 1 wherein said platinum nanoparticles are 2-10 wt % based on the weight of the carbon nanotubes loaded with the platinum nanoparticles.

* * * * *